(12) United States Patent
Xia et al.

(10) Patent No.: US 11,619,629 B2
(45) Date of Patent: Apr. 4, 2023

(54) MODIFIED CARDIOLIPIN-COATED MAGNETIC NANOBEADS AND PREPARATION METHODS THEREFOR

(71) Applicant: SHENZHEN YHLO BIOTECH CO., LTD., Shenzhen (CN)

(72) Inventors: Fuzhen Xia, Shenzhen (CN); Dingbiao Zou, Shenzhen (CN); Gang Wang, Shenzhen (CN); Xiaoqin Ye, Shenzhen (CN); Chungen Qian, Shenzhen (CN)

(73) Assignee: SHENZHEN YHLO BIOTECH CO., LTD., Shenzhen (CN)

( * ) Notice: Subject to any disclaimer, the term of this patent is extended or adjusted under 35 U.S.C. 154(b) by 1131 days.

(21) Appl. No.: 16/313,907

(22) PCT Filed: Jun. 30, 2016

(86) PCT No.: PCT/CN2016/087985
§ 371 (c)(1),
(2) Date: Dec. 28, 2018

(87) PCT Pub. No.: WO2018/000364
PCT Pub. Date: Jan. 4, 2018

(65) Prior Publication Data
US 2021/0231649 A1    Jul. 29, 2021

(51) Int. Cl.
| | | |
|---|---|---|
| G01N 33/543 | (2006.01) | |
| G01N 33/92 | (2006.01) | |
| G01N 33/531 | (2006.01) | |
| B82Y 15/00 | (2011.01) | |
| B82Y 40/00 | (2011.01) | |

(52) U.S. Cl.
CPC ....... *G01N 33/5434* (2013.01); *G01N 33/531* (2013.01); *B82Y 15/00* (2013.01); *B82Y 40/00* (2013.01)

(58) Field of Classification Search
CPC ............. G01N 33/5434; G01N 33/531; G01N 2405/04; G01N 33/54333; G01N 33/92; B82Y 15/00; B82Y 40/00; B82Y 25/00; H01F 1/0054
See application file for complete search history.

(56) References Cited

U.S. PATENT DOCUMENTS

| | | | |
|---|---|---|---|
| 2007/0111331 A1* | 5/2007 | Hong | ............... G01N 33/54326 436/526 |
| 2011/0136143 A1* | 6/2011 | Castro | .................... G01N 33/92 435/7.9 |
| 2014/0051070 A1 | 2/2014 | Arai et al. | |

FOREIGN PATENT DOCUMENTS

| | | |
|---|---|---|
| CN | 1829803 A | 9/2006 |
| CN | 101243321 A | 8/2008 |
| CN | 101360997 A | 2/2009 |
| CN | 102565405 A | 7/2012 |
| CN | 105467122 A | 4/2016 |
| WO | 2007126051 A1 | 11/2007 |
| WO | 2012122929 A1 | 9/2012 |

OTHER PUBLICATIONS

Sun et al. (Membrane-Mimetic Films of Asymmetric Phosphatidylcholine Lipid Bolaamphiphiles Langmuir, vol. 22, pp. 1201-1208, published Dec. 31, 2005) (Year: 2005).*
PubChem (Biotin, https://pubchem.ncbi.nlm.nih.gov/compound/Biotin, retrieved on May 6, 2022). (Year: 2002).*
Lisa Y. Wu et al., "Chemoaffinity Capture of Pre-Targeted Prostate Cancer Cells with Magnetic Beads", The Prostate, Oct. 2012, vol. 72, total 17 pages.

* cited by examiner

*Primary Examiner* — Shafiqul Haq
*Assistant Examiner* — Nam P Nguyen
(74) *Attorney, Agent, or Firm* — Kilpatrick Townsend & Stockton, LLP

(57) ABSTRACT

Provided in the present invention are a magnetic nanosphere coated with modified cardiolipin, and manufacturing method thereof. The magnetic nanosphere coated with modified cardiolipin comprises a modified cardiolipin, a biotin derivative, and a streptavidin magnetic bead. The modified cardiolipin is coupled to the biotin derivative via an —NH—CO structure. The streptavidin magnetic bead is a magnetic nanosphere coupled to streptavidin, and the biotin derivative is coupled to the streptavidin.

8 Claims, 1 Drawing Sheet

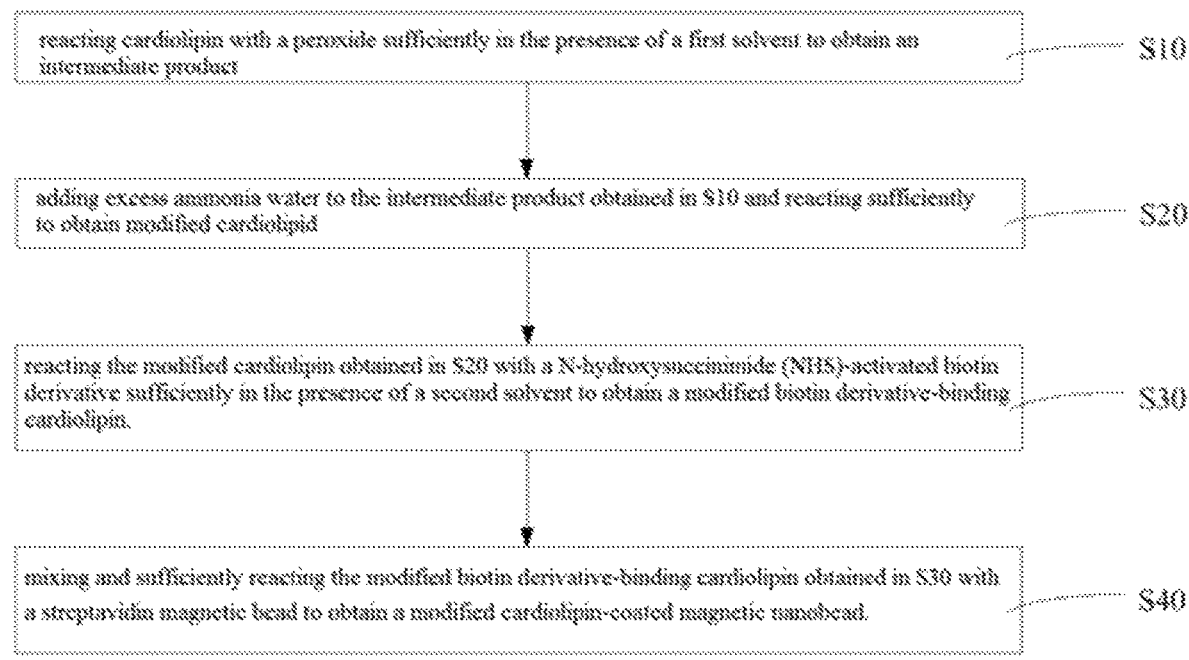

MODIFIED CARDIOLIPIN-COATED MAGNETIC NANOBEADS AND PREPARATION METHODS THEREFOR

CROSS-REFERENCE TO RELATED APPLICATIONS

This application is a National Stage of International Application No. PCT/CN2016/087985, filed on Jun. 30, 2016, which is hereby incorporated by reference in its entirety.

FIELD

The disclosure relates to the field of in vitro detection, in particular to a modified cardiolipin-coated magnetic nanobead and a method for preparing the same.

BACKGROUND

Anticardiolipin antibody is an antibody capable of reacting with a variety of antigen substances containing a phospholipid structure, and the antigen is a negatively charged phospholipid component participating in a variety of cell membrane compositions. Clinically, anticardiolipin antibody mainly exists in patients with antiphospholipid syndrome, various autoimmune diseases and syphilis infection.

Antiphospholipid syndrome (APS), including a variety of autoimmune diseases, are more common in young people, with a male-to-female incidence ratio of about 2:8. Patients may have one or more manifestations, involving multiple systems and organs and including: venous and arterial thrombosis, thrombocytopenia, habitual abortion, cardiomyopathy, heart disease, cerebral and renal infarction, and pulmonary hypertension. Malignant APS may be manifested by progressive and extensive thrombosis in a short term, leading to multiple organ failure and even death. Antiphospholipid syndrome may not only be secondary to systemic lupus erythematosus or other autoimmune diseases, but also occur alone (primary antiphospholipid syndrome).

Antiphospholipid antibodies may also be produced in a patient suffering from syphilis, a sexually transmitted disease caused by spirochete bacteria, *Treponema pallidum*. More than 5 million people are reported to be infected with syphilis each year, including 30,000 congenitally infected infants. Syphilis may be latent and hidden in patients for many years, and may lead to various clinical manifestations. Patients show no clinical symptoms in a latent period of syphilis, which lasts for life in about two-thirds of untreated patients. An infected person is not infectious during the latent period; however, a child born to a mother in the latent period may be infected with congenital syphilis.

Antiphospholipid antibody assay is widely used in the diagnosis of phospholipid syndrome and non-*treponema* test for syphilis. This assay has the advantage of inexpensively, fastly and conveniently performing on a large number of samples. In addition, since the antiphospholipid antibody has a concentration that will gradually decrease with successful treatment of syphilis, and a high level of treponemal antibody, which is a specific antibody to syphilis infection, will last for several years or even for life. Therefore, the antiphospholipid antibody assay is considered to be a better choice for monitoring the treatment of syphilis.

A main conventional method of detecting an antiphospholipid antibody is to coat cardiolipin by physical adsorption onto a specific solid, such as an ELISA plate, and then binding the antiphospholipid antibody in a sample to be detected with cardiolipin attached to the ELISA plate, thereby achieving the capture of the antiphospholipid antibody in the sample. The concentration of the antiphospholipid antibody in the sample can be indirectly read by allowing the color development of the captured antiphospholipid antibody and measuring a concentration for luminescence.

Since cardiolipin immobilized by physical adsorption is easily dissociated and detached from the solid plate under an influence of external conditions, such as a solvent, heating and the like, a test product prepared by this method has poor stability.

SUMMARY

Based on this, it is necessary to provide a well-stabilized modified cardiolipin-coated magnetic nanobead for detecting an anticardiolipin antibody and a method for preparing the same.

A modified cardiolipin-coated magnetic nanobead comprises: a modified cardiolipin, a biotin derivative and a streptavidin magnetic bead;

the modified cardiolipin is obtained by oxidizing and aminating a hydrophobic fatty acid side chain of cardiolipin, and the modified cardiolipin contains -$NH_2$;

the biotin derivative has a structural formula of

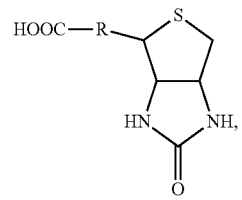

wherein —R— is a saturated alkyl chain having 4 to 20 carbon atoms or a polyethylene glycol chain having 2 to 10 carbon atoms, —$NH_2$ in the modified cardiolipin and COOH in the biotin derivative form a —NH—CO— structure to link the modified cardiolipin and the biotin derivative together;

the streptavidin magnetic bead is a streptavidin-binding magnetic nanobead, and the biotin derivative is linked to streptavidin.

A method for preparing the above modified cardiolipin-coated magnetic nanobead comprises:

reacting cardiolipin with a peroxide sufficiently in the presence of a first solvent to obtain an intermediate product;

adding excess ammonia water to the intermediate product and reacting sufficiently to obtain a modified cardiolipid, wherein a hydrophobic fatty acid side chain of the modified cardiolipin is oxidized and aminated, and the modified cardiolipin contains an amino group;

reacting the modified cardiolipin with a N-hydroxysuccinimide-activated biotin derivative sufficiently in the presence of a second solvent to obtain a modified biotin derivative-binding cardiolipin, wherein the biotin derivative has a structural formula of

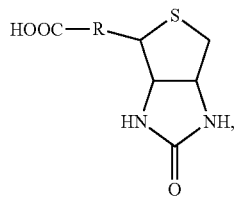

wherein —R— is a carbon chain having 4 to 20 carbon atoms or a polyethylene glycol chain having 2 to 10 carbon atoms, —NH$_2$ in the modified cardiolipin and —COOH in the biotin derivative form a —NH—CO— structure to link the modified cardiolipin and the biotin derivative together, thereby producing a modified biotin derivative-binding cardiolipin; and mixing and sufficiently reacting the modified biotin derivative-binding cardiolipin with a streptavidin magnetic bead to obtain the modified cardiolipin-coated magnetic nanobead, wherein the streptavidin magnetic bead is a streptavidin-binding magnetic nanobead, and the biotin derivative is linked to streptavidin.

Such a modified cardiolipin-coated magnetic nanobead with direct and strong linkages by chemical bonds between the modified cardiolipin and the biotin derivative and between the biotin derivative and streptavidin on a surface of the streptavidin magnetic bead enables easier control of an amount of modified cardiolipin on the surface of magnetic bead than that in the physical absorption manner, and allows to control the amount of modified cardiolipin and a distance between the magnetic nanobeads by adjusting a length of —R—, so that the amount of modified cardiolipin and a space for binding to an antiphospholipid antibody are better retained. The modified cardiolipin-coated magnetic nanobead can be directly used for the detection of antiphospholipid antibodies, and have higher stability than test products prepared by the conventional method for physically adsorbing cardiolipin.

BRIEF DESCRIPTION OF THE DRAWINGS

FIG. 1 is a flowchart of a method for preparing a modified cardiolipin-coated magnetic nanobead according to an embodiment.

DETAILED DESCRIPTION OF THE INVENTION

In order to make the above objects, features and advantages of the present disclosure more clearly understood, specific embodiments of the present disclosure will be described in detail with reference to the accompanying drawings and specific examples. Numerous specific details are set forth in the following description in order to facilitate a thorough understanding of the disclosure. But the disclosure can be practiced in many other ways than those described herein, and those skilled in the art can make similar improvements without departing from the spirit of the disclosure, and therefore the disclosure is not limited by the specific implementation disclosed below.

In an embodiment, a modified cardiolipin-coated magnetic nanobead includes a modified cardiolipin, a biotin derivative and a streptavidin magnetic bead.

Cardiolipin, an ester composed of 3 glycerol, 2 phosphoric acid and 4 unsaturated long chain alkyl groups, has a structure containing 2 hydrophilic cores and 4 hydrophobic side chains. Cardiolipin has a structural formula as follows:

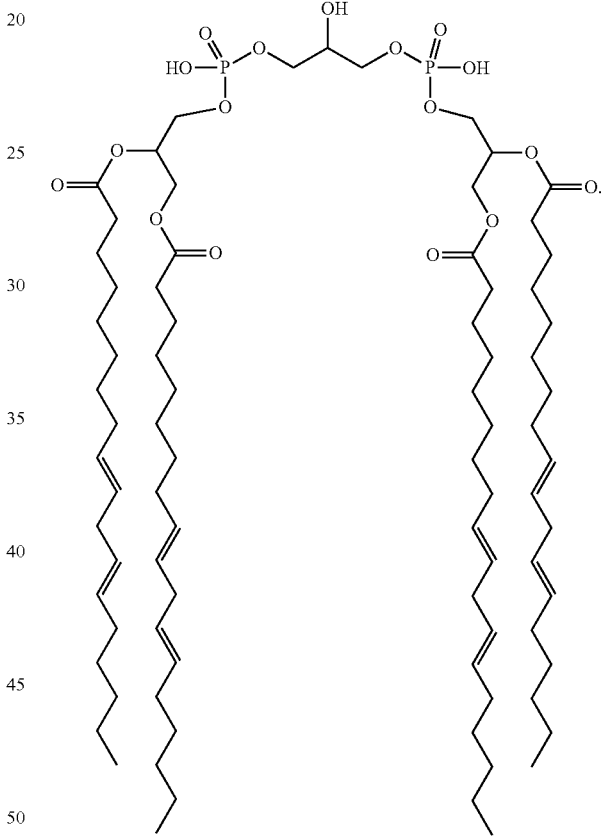

The modified cardiolipin is obtained by oxidizing and aminating a hydrophobic fatty acid side chain of cardiolipin, and contains NH$_2$.

Since cardiolipin has four side chains, which may be simultaneously oxidized when cardiolipin is modified, the modified cardiolipin may contain a plurality of NH$_2$. In particular, the modified cardiolipin may comprise 1 to 8 NH$_2$.

Preferably, the modified cardiolipin contains one NH$_2$.

Particularly preferably, the modified cardiolipin has a structural formula as follows:

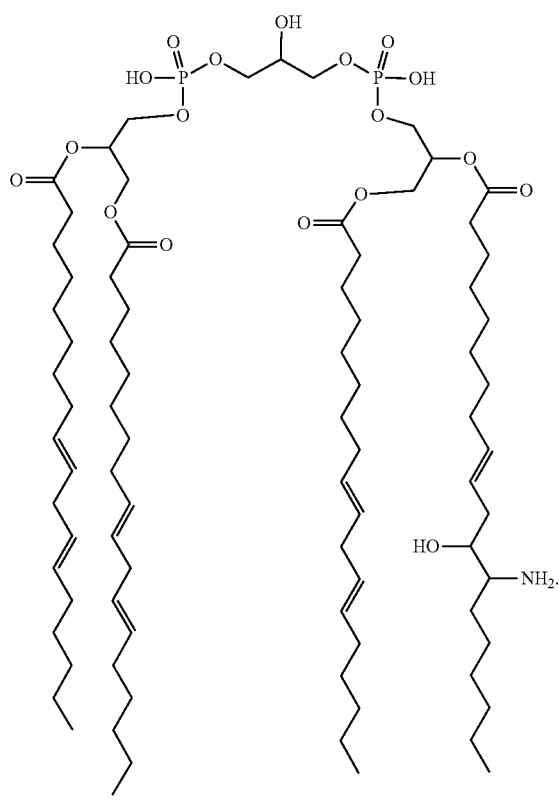 [SMILES: CCCCC/C=C/C/C=C/CCCCCCCC(=O)OCC(COP(=O)(O)OCC(O)COP(=O)(O)OCC(COC(=O)CCCCCCC/C=C/C/C=C/CCCCC)OC(=O)CCCCCCC/C=C/CC(O)C(N)CCCCCC)OC(=O)CCCCCCC/C=C/C/C=C/CCCCC]

The biotin derivative has a structural formula of

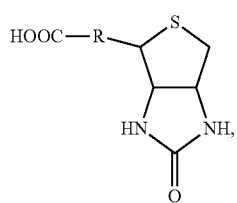

wherein —R— is a saturated alkyl chain having 4 to 20 carbon atoms or a polyethylene glycol chain having 2 to 10 carbon atoms.

$NH_2$ in the modified cardiolipin and —COOH in the biotin derivative form a —NH—CO-structure to link the modified cardiolipin and the biotin derivative together.

Preferably, —R— is a saturated alkyl chain containing 4 to 10 carbon atoms.

Particularly preferably, —R— is —$(CH_2)_6$—.

Since cardiolipin has a very small molecule size and a seriously insufficient space for modification, the modification of hydrophilic phosphate core will cause a reduced affinity of cardiolipin to antiphospholipid antibody, and even loss of antigenic activity.

The modified cardiolipin at the hydrophilic phosphate core of cardiolipin is retained in the modified cardiolipin-coated magnetic nanobead by modifying the hydrophobic side chain of cardiolipin.

Such a modified cardiolipin-coated magnetic nanobead with direct and strong linkages by chemical bonds between the modified cardiolipin and the biotin derivative and between the biotin derivative and streptavidin on a surface of the streptavidin magnetic bead enables easier control of an amount of modified cardiolipin on the surface of magnetic bead than that in the physical absorption manner, and allows to control the amount of modified cardiolipin and a distance between the magnetic nanobeads by adjusting a length of —R—, so that the amount of modified cardiolipin and a space for binding to an antiphospholipid antibody are better retained. The modified cardiolipin-coated magnetic nanobead can be directly used for the detection of antiphospholipid antibodies, and have higher stability than test products prepared by the conventional method for physically adsorbing cardiolipin.

In addition, since each streptavidin can be tightly bound to 4 biotins, such a modified cardiolipin-coated magnetic nanobead allows a detected signal to be amplified 4 times through biotin-streptavidin amplification effect, greatly improving sensitivity for detecting an antiphospholipid antibody.

As shown in FIG. 1, the method for preparing the above modified cardiolipin-coated magnetic nanobead comprises:

S10, reacting cardiolipin with a peroxide sufficiently in the presence of a first solvent to obtain an intermediate product.

A fatty acid side chain of cardiolipin is oxidized by reaction of cardiolipin with the peroxide.

The peroxide is peroxybenzoic acid, m-chloroperoxybenzoic acid, peroxyacetic acid, or peroxypropionic acid.

A molar ratio of cardiolipin to peroxide ranges from 1:1 to 1:8.

The first solvent is dichloromethane, trichloromethane, chloroform, benzene, or toluene.

In S10, an operation for purifying an intermediate product is further included, and the purifying may be performed by preparative liquid chromatography after extraction with ethyl acetate. After purification, modified cardiolipin having a purity of about 80% may be obtained.

In S10, the reaction is performed at a temperature ranging from 60° C. to 100° C.

In S20, adding excess ammonia water to the intermediate product obtained in S10 and reacting sufficiently to obtain modified cardiolipin.

The hydrophobic fatty acid side chain of cardiolipin is oxidized and aminated by the peroxide and ammonia water, so that the modified cardiolipin prepared contains an amino group.

Since cardiolipin has four side chains, which may be simultaneously oxidized when cardiolipin is modified, the modified cardiolipin may contain a plurality of amino groups. In particular, the modified cardiolipin may comprise 1 to 8 —$NH_2$.

Preferably, the modified cardiolipin contains one —$NH_2$.

Particularly preferably, the modified cardiolipin has a structural formula as follows:

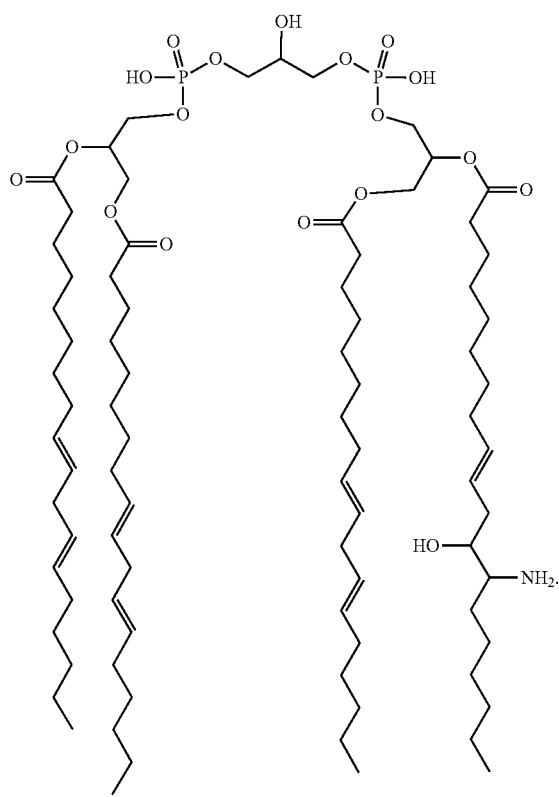 [SMILES: CCCCC/C=C/C/C=C/CCCCCCCC(=O)OCC(COP(=O)(O)OCC(O)COP(=O)(O)OCC(COC(=O)CCCCCCC/C=C/C/C=C/CCCCC)OC(=O)CCCCCCC/C=C/CC(O)C(N)CCCCCC)OC(=O)CCCCCCC/C=C/C/C=C/CCCCC]

Ammonia water has a mass concentration ranging from 10% to 30%.

In S20, the reaction is performed at a temperature ranging from 60° C. to 100° C.

S30, reacting the modified cardiolipin obtained in S20 with a N-hydroxysuccinimide (NHS)-activated biotin derivative sufficiently in the presence of a second solvent to obtain a modified biotin derivative-binding cardiolipin.

The biotin derivative has a structural formula of

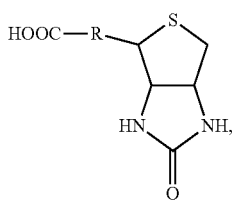

—R— is a carbon chain having 4 to 20 carbon atoms or a polyethylene glycol chain having 2 to 10 carbon atoms, —$NH_2$ in the modified cardiolipin and —COOH in the biotin derivative form a —NH—CO— structure to link the modified cardiolipin and the biotin derivative together, thereby producing a modified biotin derivative-binding cardiolipin.

Preferably, —R— is a saturated alkyl chain containing 4 to 10 carbon atoms.

Particularly preferably, —R— is —$(CH_2)_6$—.

The NHS-activated biotin derivative, i.e. biotin derivative NHS ester, may be directly obtained commercially.

In 530, the second solvent is DMSO, DMF, tetrahydrofuran, or phosphate-buffered saline having a pH of 6.5 to 8.5.

In 530, a molar ratio of the modified cardiolipin to the N-hydroxysuccinimide-activated biotin derivative ranges from 1:1.5 to 1:20.

S40, mixing and sufficiently reacting the modified biotin derivative-binding cardiolipin obtained in S30 with a streptavidin magnetic bead to obtain a modified cardiolipin-coated magnetic nanobead.

The streptavidin magnetic bead is a streptavidin-binding magnetic nanobead, and the biotin derivative is linked to streptavidin.

The Streptavidin magnetic bead can be directly obtained commercially, for example, from MagnaBind Corporation.

In the operation for mixing and sufficiently reacting the modified biotin derivative-binding cardiolipin with the streptavidin magnetic bead, the modified biotin derivative-binding cardiolipin has a concentration of 0.1 mg/mL to 1 mg/mL, and the streptavidin magnetic bead has a concentration of 5 mg/mL to 15 mg/mL.

Such a method for preparing a modified cardiolipin-coated magnetic nanobead with direct and strong linkages by chemical bonds between the modified cardiolipin and the biotin derivative and between the biotin derivative and streptavidin on a surface of the streptavidin magnetic bead enables easier control of an amount of modified cardiolipin on the surface of magnetic bead than that in the physical absorption manner, and allows to control the amount of modified cardiolipin and a distance between the magnetic nanobeads by adjusting a length of —R—, so that the amount of modified cardiolipin and a space for binding to an antiphospholipid antibody are better retained. The modified cardiolipin-coated magnetic nanobead thus prepared can be directly used for the detection of antiphospholipid antibodies, and have higher stability than test products prepared by the conventional method for physically adsorbing cardiolipin.

In addition, since each streptavidin can be tightly bound to 4 biotins, the modified cardiolipin-coated magnetic nanobead prepared allows a detected signal to be amplified 4 times through biotin-streptavidin amplification effect, greatly improving sensitivity for detecting an antiphospholipid antibody.

Specific examples are as follows.

Example 1: Preparation of Modified Cardiolipin

Under argon protection, 0.5 mmol of cardiolipin was dissolved in 1 mL of anhydrous toluene, to which 1.5 mmol of m-chloroperoxybenzoic acid was added, and the temperature was gradually heated to 110° C. while stirring. The mixture was reacted at 110° C. for 72 hours, and was poured into 25 mL of ice water after cooled to room temperature. The resulting solution was extracted three times with 20 mL of ethyl acetate, and ethyl acetate phases were combined. The combined ethyl acetate phase was washed once with 10 mL of a saturated sodium chloride solution and dried over anhydrous sodium sulfate for 12 hours. Ethyl acetate was evaporated to dryness in vacuo. Residual solid was added to 8 mL of concentrated ammonia water. The resulting mixture was gradually heated to 100° C. with stirring and reacted for 8 hours. The reaction solution was evaporated to dryness in vacuo to obtain a yellow viscous liquid. 1, and the insoluble material, after dissolved in a small amount of methano, was filtered off with 0.2 μm filter membrane. The filtrate was purified by preparative liquid chromatography to obtain about 83 mg of white solid (S(ESI+, m/z): 1495.29113).

Example 2: Preparation of Modified Biotin Derivative-Binding Cardiolipin 50 mg of modified cardiolipin prepared in Example 1 was weighed and dissolved in 2 mL of anhydrous DMF. 20 mg of biotin derivative NHS ester was added under stirring, and the reaction was performed for 2.5 hours at room temperature. The reaction solution was evaporated to dryness in vacuo. Residual solid was dissolved in 5 mL of ethyl acetate, insoluble material was filtered off, and the obtained ethyl acetate solvent was evaporated to dryness to obtain a modified biotin derivative-binding cardiolipin as a white solid.

In this example, the biotin derivative has a structural formula of

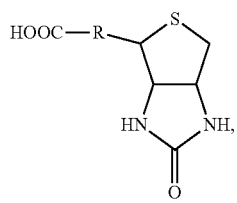

and —R— is —$(CH_2)_6$—.

The modified biotin derivative-binding cardiolipin prepared in this example may be ready for later use without special purification.

Example 3: Preparation of Modified Cardiolipin-Coated Streptavidin Magnetic Nanobead To 100 μL of 0.2 mg/mL modified biotin derivative-binding cardiolipin in phosphate-buffered saline was added 100 μL of 10 mg/mL streptavidin magnetic beads, and after homogeneous mixing, the mixture was incubated at 37° C. for 10 minutes. After magnetic separation, 1 mL of 30 mM Tris buffer was used for redissolution, and the mixture obtained by redissolution was shaken and then magnetically separated again. The obtained solid was redissolved in 5 mL of 30 mM Tris buffer to give a solution of 0.02 mg/mL modified cardiolipin-coated streptavidin magnetic nanobead.

Example 4: Reaction of Modified Cardiolipin-Coated Streptavidin Magnetic Bead with an Antiphospholipid Sample To 200 μL of each solution of modified cardiolipin-coated streptavidin magnetic nanobead prepared in Examples 1 to 3 was added 5 μL of antiphospholipid antibody serum sample and the mixture was incubated at 37° C. for 30 minutes. After magnetic separation, the modified cardiolipin-coated streptavidin magnetic nanobead was redissolved in 200 μL, and a horseradish peroxidase-labeled secondary antibody was added, and after incubation at 37° C. for 30 minutes, the mixture was sequentially washed, blended with a TMB substrate solution and incubated for 10 minutes. Then, 100 μL of stop solution was added and OD value was read on the microplate reader within 10 minutes to obtain a luminescence signal value of the sample.

Three cardiolipin-positive serum samples and three cardiolipin-negative serum samples were measured respectively for OD values, and the magnetic bead prepared by conventional physical adsorption method is used as a control for comparing the measured OD values, which are shown in the following Table 1.

TABLE 1 measured OD values of different samples in Examples 1 to 3 and control group (physical adsorption method)

| Sample number | Negative sample 1 | Negative sample 2 | Negative sample 3 | Positive sample 1 | Positive sample 2 | Positive sample 3 |
| --- | --- | --- | --- | --- | --- | --- |
| Example 1 | 59 | 74 | 64 | 1764 | 2783 | 2577 |
| Example 2 | 62 | 85 | 73 | 2148 | 3152 | 2991 |
| Example 3 | 41 | 59 | 47 | 1533 | 2566 | 2853 |
| control group | 153 | 371 | 293 | 599 | 861 | 765 |

As can be seen from table 1, in the detection of antiphospholipid antibody samples, the luminescence signal of the modified cardiolipin-coated streptavidin magnetic nanobead prepared in Examples 1 to 3 is significantly decreased (by 1 to 4 folds) when measuring the negative samples, and tremendously increased (by 3 to 10 folds) when measuring the positive samples, compared to that of the magnetic bead prepared by physical adsorption method (the control group).

Thus, the modified cardiolipin-coated streptavidin magnetic nanobead prepared in Examples 1 to 3 had significantly improved sensitivity for detecting an antiphospholipid sample compared to the magnetic bead made by conventional physical adsorption method.

The examples described above only show one or more embodiments of the present disclosure, the description of which is more specific and detailed, but is not therefore to be understood as limiting the scope of the disclosure. It should be noted that for those of ordinary skill in the art, several variations and modifications may also be made without departing from the inventive concept, which are within the scope of the present disclosure. Therefore, the scope of protection of this disclosure shall be subject to the appended claims.

The invention claimed is:

1. A modified cardiolipin-coated magnetic nanobead comprises: a modified cardiolipin, a biotin derivative and a streptavidin magnetic bead;
    the modified cardiolipin is obtained by oxidizing and aminating a hydrophobic fatty acid side chain of cardiolipin, and the modified cardiolipin has a structural formula as follows:

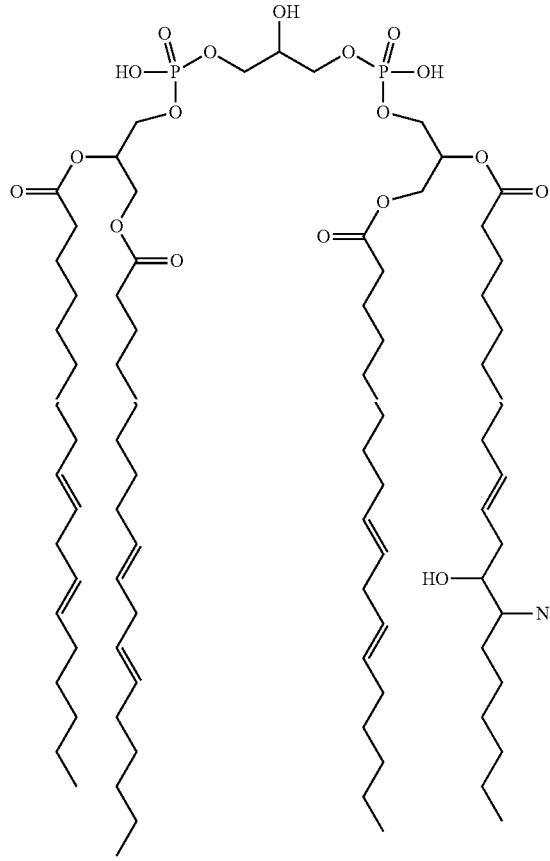

The biotin derivative has a structural formula of

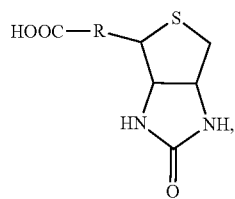

wherein —R— is a saturated alkyl chain having 4 to 20 carbon atoms or a polyethylene glycol chain having 2 to 10 carbon atoms, —NH$_2$ in the modified cardiolipin and —COGH in the biotin derivative form a —NH—CO— structure to link the modified cardiolipin and the biotin derivative together;

the streptavidin magnetic bead is a streptavidin-binding magnetic nanobead, and the biotin derivative is linked to streptavidin.

2. The modified cardiolipin-coated magnetic nanobead according to claim 1, wherein the —R— is a saturated alkyl chain containing 4 to 10 carbon atoms.

3. A method for preparing the modified cardiolipin-coated magnetic nanobead according to claim 1, comprises:

reacting cardiolipin with a peroxide sufficiently in the presence of a first solvent to obtain an intermediate product;

adding excess ammonia water to the intermediate product and reacting sufficiently to obtain the modified cardiolipin, wherein a hydrophobic fatty acid side chain of the modified cardiolipin is oxidized, and the modified cardiolipin has a structural formula as follows:

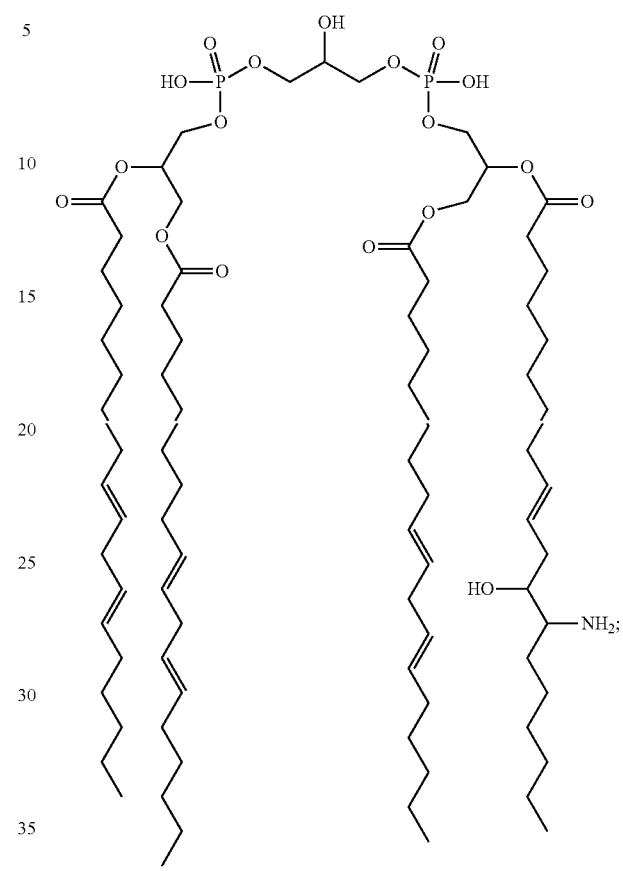

reacting the modified cardiolipin with a biotin derivative sufficiently in the presence of a second solvent to obtain a modified biotin derivative-binding cardiolipin, where the biotin derivative has a structural formula of

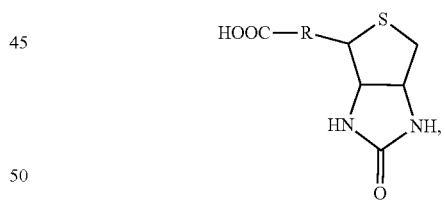

wherein —R— is a carbon chain having 4 to 20 carbon atoms or a polyethylene glycol chain having 2 to 10 carbon atoms, —NH$_2$ in the modified cardiolipin and COOH in the biotin derivative form a —NH—CO— structure to link the modified cardiolipin and the biotin derivative together, thereby producing a modified biotin derivative-binding cardiolipin; and mixing and sufficiently reacting the modified biotin derivative-binding cardiolipin with a streptavidin magnetic bead to obtain the modified cardiolipin-coated magnetic nanobead, wherein the streptavidin magnetic bead is a streptavidin-binding magnetic nanobeads, and the biotin derivative is linked to streptavidin.

4. The method according to claim 3, wherein the peroxide is peroxybenzoic acid, m-chloroperoxybenzoic acid, peroxyacetic acid, or peroxypropionic acid, a molar ratio of cardiolipin to the peroxide ranges from 1:1 to 1:8, and the first solvent is dichloromethane, trichloromethane, chloroform, benzene, or toluene, in the operation for reacting cardiolipin with the peroxide sufficiently in the presence of the first solvent.

5. The method according to claim 3, wherein ammonia water has a mass concentration ranging from 10% to 30% in the operation for adding excess ammonia water to the intermediate product and reacting sufficiently.

6. The method according to claim 3, wherein the second solvent is DMSO, DMF, tetrahydrofuran, or phosphate-buffered saline having a pH of 6.5 to 8.5 in the operation for reacting the modified cardiolipin with the N-hydroxysuccinimide-activated biotin derivative sufficiently in the presence of the second solvent.

7. The method according to claim 3, wherein a molar ratio of the modified cardiolipin to the N-hydroxysuccinimide-activated biotin derivative ranges from 1:1.5 to 1:20 in the operation for reacting the modified cardiolipin with the N-hydroxysuccinimide-activated biotin derivative sufficiently in the presence of the second solvent.

8. The method according to claim 3, wherein the modified biotin derivative-binding cardiolipin has a concentration of 0.1 mg/mL to 1 mg/mL, and the streptavidin magnetic bead has a concentration of 5 mg/mL to 15 mg/mL in the operation for mixing and sufficiently reacting the modified biotin derivative-binding cardiolipin with the streptavidin magnetic bead.

* * * * *